United States Patent
Erlen et al.

(10) Patent No.: US 12,186,527 B2
(45) Date of Patent: Jan. 7, 2025

(54) LOCKING MECHANISM FOR A MODULAR ORGANIZATION SYSTEM

(71) Applicant: B. Braun Melsungen AG, Melsungen (DE)

(72) Inventors: Christoph Erlen, Kassel (DE); Hans-Josef Gerlach, Marsberg (DE); Andreas Schüssler, Kassel (DE); Thomas Spörl, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 957 days.

(21) Appl. No.: 17/274,322

(22) PCT Filed: Sep. 19, 2019

(86) PCT No.: PCT/EP2019/075217
§ 371 (c)(1),
(2) Date: Mar. 8, 2021

(87) PCT Pub. No.: WO2020/058428
PCT Pub. Date: Mar. 26, 2020

(65) Prior Publication Data
US 2021/0322673 A1    Oct. 21, 2021

(30) Foreign Application Priority Data
Sep. 19, 2018 (DE) ............. 10 2018 122 994.1

(51) Int. Cl.
*A61M 5/14* (2006.01)
*A61M 5/50* (2006.01)

(52) U.S. Cl.
CPC ........ *A61M 5/1413* (2013.01); *A61M 5/1408* (2013.01)

(58) Field of Classification Search
CPC .............. A61M 5/1413; A61M 5/1408; A61M 5/1407; A61M 5/16827; A61M 5/50; A61M 2005/3142; A61M 2039/0229
See application file for complete search history.

(56) References Cited

U.S. PATENT DOCUMENTS

| 5,836,910 A | 11/1998 | Duffy et al. |
| 2007/0088249 A1* | 4/2007 | Duffy ............... G16H 10/60 604/65 |

(Continued)

FOREIGN PATENT DOCUMENTS

| CA | 2390517 A1 | 5/2001 |
| CN | 203677636 U | 7/2014 |

(Continued)

OTHER PUBLICATIONS

German Search Report received in Application No. 10 2018 122 994.1 dated Dec. 7, 2018, 14 pages.

(Continued)

*Primary Examiner* — Robert J Utama
*Assistant Examiner* — Hamza A Darb
(74) *Attorney, Agent, or Firm* — Christopher A. Rothe; CM Law (57) ABSTRACT

A modular arrangement system for arranging medical devices, in particular infusion pumps, and a device having a housing which forms the modular arrangement system. The system has at least two arrangement modules which can be mechanically connected to one another. A first arrangement module has a first housing part with a first coupling structure arranged on at least two diametrically opposed sides. A second arrangement module has a second housing part adapted to be mounted on, below or laterally to the first housing part. The second housing part has a bar rotatably or slidably mounted in the second housing part for locking the two housing parts. The bar is designed in such a way that, (Continued)

by a singular actuation, it engages into the first coupling structure on at least two diametrically opposite sides of the first housing part, preferably simultaneously in an undercutting manner.

19 Claims, 7 Drawing Sheets

(56) References Cited

U.S. PATENT DOCUMENTS

2013/0281965 A1* 10/2013 Kamen .................. G16H 20/17
                                                              604/67
2015/0157791 A1    6/2015 Desch et al.

FOREIGN PATENT DOCUMENTS

| DE | 69929828    | 10/2006 |
| DE | 69935622 T2 | 12/2007 |
| EP | 0780134 A1  | 6/1997  |
| WO | 9856450 A1  | 12/1998 |
| WO | 0136027 A1  | 5/2001  |

OTHER PUBLICATIONS

International Search Report received in Application No. PCT/EP2019/075217 dated Dec. 6, 2019, 5 pages.
Written Opinion received in Application No. PCT/EP2019/075217 dated Dec. 6, 2019, 12 pages.

* cited by examiner

LOCKING MECHANISM FOR A MODULAR ORGANIZATION SYSTEM

CROSS-REFERENCE TO RELATED APPLICATION(S)

This application is the United States national phase entry of International Application No. PCT/EP2019/075217, filed Sep. 19, 2019, and claims the benefit of priority of German Application No. 10 2018 122 994.1, filed Sep. 19, 2018. The contents of International Application No. PCT/EP2019/075217 and German Application No. 10 2018 122 994.1 are incorporated by reference herein in their entireties.

FIELD

The present invention relates to a modular arrangement system for arranging medical devices and a medical device having a housing which forms the modular arrangement system, comprising at least two arrangement modules which can be mechanically connected to one another, wherein a first arrangement module has a first housing part on which a first coupling structure is provided on at least two diametrically opposed sides, and a second arrangement module has a second housing part which is adapted to be mounted/coupled on, below or laterally to the first housing part of the first arrangement module and comprises a bar rotatably or slidably mounted in the second housing part for locking the two housing parts.

BACKGROUND

In the medical therapeutic environment, several different instruments are often interconnected.

One example is represented by infusion pumps for the intravenous administration of drugs or nutrients, which are indispensable in areas such as operating theatres, intensive care units, oncology, pain therapy, clinical nutrition, etc. Single infusion pumps as well as systems consisting of several interconnected infusion pumps can be used here, which can be adjusted for the infusion of different substances and dosages as well as specifically for different infusion therapies. In order to simplify the interconnection of different devices, especially infusion pumps, there are various arrangement systems/rack systems. This is where the present invention comes in. The present disclosure relates to arrangement systems of modular construction for mechanically coupling medical devices, especially infusion pumps.

It is generally known from prior art, e.g. from U.S. Pat. No. 4,756,706 (A), that infusion pumps are clamped or hung one above the other on rod-like or shelf-type supports. Such systems make it possible to nearly arbitrarily combine, add or remove several infusion pumps and to transport the combined pumps easily if necessary. However, the disadvantage is that such shelf or rod supports require a lot of space, have high storage costs and can become unstable depending on the load. In addition, clamps for fixing the pumps to the corresponding support may have to withstand high forces and torques.

Further, EP 0 780 134 A1 discloses that several infusion systems can be stacked directly on top of each other. Here, two modules are hooked into each other on a first side in such a way that the hook-type connection acts as a hinge around which the modules can be pivoted to each other in a hinge-like manner. They are then locked on an opposite second side. In order to connect two modules with each other, they must be placed carefully in a time-consuming way. The locking structure is relatively complex and also has an integrated electrical connection, which is why the cleaning of the components needs a lot of time. Moreover, a part of the locking mechanism on the second side consists of a hook which, due to the complex design of the locking mechanism, must take up little space and is of very narrow design. The resulting locking mechanism is thus limited almost in punctiform manner to one corner of the pump, which limits the stability of the connection. Furthermore, it may happen that two modules are placed on top of each other, but then locking them is forgotten, making the stack unstable, which can endanger the safe performance of a therapy or operation and can also lead to injuries of the operating staff.

CN 203 677 636 U also discloses stackable medical pumps, wherein feet of a first pump form rails into which a ledge on top of a second pump is inserted, thereby pushing away a spring-mounted bar arranged in protected fashion between the pumps, which snaps in place after reaching the stacking position and thus represents an automatic safety device. Nevertheless, it can happen that the pumps are not stacked correctly in undetected manner, the bar does not snap in place and the stacking is unstable. Furthermore, the feet can easily get stuck in the rails, or at least are not pushed in and out evenly and without jolting. When the connection is released, the bar has to be pressed down again and the pumps have to be shifted relative to each other at the same time, which is cumbersome and poses the risk of the staff getting their hand caught between the pumps due to the fact that the bar is located between the pumps and is not easily accessible. In addition, the inward facing rails provided on the underside of the pump may be difficult to access and therefore difficult to clean.

SUMMARY

The object to be achieved in relation to the prior art is therefore to provide an arrangement system for medical devices to be connected to each other, in particular infusion pumps, which avoids the disadvantages described above. In particular, an arrangement system is to be provided which makes it possible to mechanically couple several arrangement modules or devices to each other in a quick, simple, intuitive, safe and space-saving manner.

The object is achieved in particular by a modular arrangement system for arranging medical devices, especially infusion pumps, with at least two mechanically connectable arrangement modules. A first arrangement module has a first housing part on which a first coupling structure is provided on at least two diametrically opposite sides. A second arrangement module has a second housing part, which is adapted to be mounted on, below or laterally to the first housing part of the first arrangement module, and which has a bar/yoke for locking the complementary housing parts rotatably and/or slidably mounted in the second housing part. The bar is designed in such a way that, by a singular actuation, it engages in an undercutting manner with the first coupling structure on at least two diametrically opposite sides of the first housing part of the first arrangement module, preferably at the same time.

In this context, singular actuation means that only a single handling or movement is required to actuate the bar with one hand. The one-handed movement performed here is a single, coherent movement and not a sequence of movements.

Thus, the arrangement modules of the arrangement system according to the invention can be locked simply and intuitively.

Although the arrangement system is advantageously designed for coupling, especially stacking, of infusion pumps, this is not intended to be restrictive, as it can be likewise used for a variety of other devices or device combinations that are to be arranged in rack-like manner.

In principle, the arrangement system can be a rack or shelf structure by means of which a number of medical devices can be mechanically and, a, electrically coupled, advantageously in the form of a space-saving, ergonomically accessible device tower consisting of vertically stacked and locked devices. Each arrangement module can be regarded as a compartment in which one or more devices can be inserted and connected. It is advantageous if each arrangement module serves as a docking station for the device inserted therein, into which the device can easily be deposited and the relevant contacts are made at a defined position during deposition of the device, without having to make further connections by hand. In addition, such an arrangement system makes it possible to prepare a defined combination of devices for various applications and to transport them easily and safely, wherein the walls of the arrangement systems can also serve as protection for the devices inserted therein. On the other hand, this arrangement system also allows individual pumps to be replaced in the fully prepared device tower, for example in the event of a defect, for maintenance purposes, or for refilling or replacing any existing containers.

As an alternative to the shelf-type design of the arrangement system described above, the arrangement modules may be connected directly to the devices to be coupled. This means that the housing parts of the arrangement modules are at the same time part of the housings of the devices to be coupled, or are alternatively adapted to be attached to the devices, so that a device can only be removed from the device tower if the entire associated arrangement module is removed.

On individual or all arrangement modules, holders or compartments for accessories, such as medicine bags or measuring devices, can be provided for the devices which are coupled or can be coupled. Furthermore, the arrangement modules may be identical to each other or have a special design in terms of specific functions as long as the coupling sides on which the two arrangement modules are connected (or supposed to be connected) are compatible with each other. Compatible electronic interfaces for data and/or power transmission may also be provided on the coupling sides of the modules.

The first coupling structure of the one arrangement module is intended to come into undercutting engagement with the bar of the other arrangement module. For example, the first coupling structure is formed as one or more projections such as hooks or ribs, or by one or more recesses such as grooves, gaps or holes. During a locking movement, the bar engages behind the first coupling structure, whereby a contact surface of the bar comes into contact with a contact surface of the coupling structure. This prevents the two arrangement modules from moving away from each other in a locked state, at least in one direction perpendicular to the abutting contact surfaces. In the example of the device tower mentioned above, the locking mechanism is configured to prevent the individual arrangement modules from moving away from each other in vertical direction. The bar can be brought into a locking position or locking status by swiveling it about a rotary axis or also by moving it in a locking direction or by a combined swiveling/linear movement. The bar can be realized, for example, in the form of one or more coupled bolts, beams or hooks. Alternatively or additionally, the bar may be able to be manually operated in one direction and spring-operated in the other direction.

According to the invention, the bar engages in the first coupling structure on at least two diametrically opposite sides of the first housing part. In this way, it can be ensured that the two housing parts are completely interlocked and securely withstand any tilting torques between the two arrangement modules. Diametrically opposite to each other refers to two positions of an arrangement module which are opposite to each other over its axis or planes of symmetry, and in the case of a rectangular module this means in particular two or four corners or side center points opposite to each other over its axis of symmetry. The positions may be situated on the coupling side or directly next to the coupling side on adjacent side surfaces of the arrangement modules.

If the two arrangement modules are mounted on top of each other according to the example of the device tower, the dead weight of the upper arrangement module helps to join them. In particular, the housing parts may have complementary structures that engage with one another during joining/assembly, which prevent the arrangement modules from a relative movement in directions other than that where the locking mechanism acts (i.e., lateral directions in the example of the device tower), which is also facilitated by the dead weight of the upper module.

Preferably, each of the at least two arrangement modules has both the first and the second housing part and each arrangement module can be coupled to any further arrangement module. In this way, the arrangement modules can be stacked in any order and in almost unlimited number.

Preferably, the first coupling structure has a raster of first protrusions and the bar has a second coupling structure with a complementary raster of second protrusions adapted to engage the first protrusions in an undercut manner.

In this way, the coupling structures are evenly distributed over the available area, in particular the first coupling structure along two side edges of the coupling side of the first arrangement module and the second coupling structure along two side edges of the bar, which allows an almost ideally distributed transmission of force and torque (in particular of the tilting torque). Preferably, at least 2 times 2 second protrusions are present or a number of second protrusions, e.g. 2 times 9, are present, which number is adapted to the size of the available area and to the expected mechanical loads. Thus, the individual ribs do not have to protrude by a large extent and the bar does not have to be excessively thick in height direction in order to achieve the required stability. The locking mechanism of the two arrangement modules can therefore withstand high mechanical forces. The bar can be made of a metal, e.g. stainless steel, or an optionally glass-fiber reinforced technical plastic, e.g. POM or PEI, which has the necessary strength as well as resistance to cleaning agents and disinfectants required for the application. Due to the simple geometry of the bar, it is easy to manufacture and clean.

The first protrusions are preferably arranged side by side, i.e. in at least one row on at least two diametrically opposite sides of the coupling side. Accordingly, in this case the second protrusions are also arranged next to each other in at least one row at positions matching the first protrusions. Here, the first and second protrusions have a defined maximum width and a defined minimum distance to each other in their direction of arrangement. The first and second coupling structure is thus essentially comb-like. This maximum width and this minimum distance correspond to each other and determine a defined raster dimension on which the raster is based.

Preferably, the bar, further preferably being of U-shaped design, can be moved linearly by a defined distance, for example between 3 and 10 mm, preferably by 5 mm, wherein the raster or raster dimension of the first and second protrusions determines the defined distance. Advantageously, the first coupling structure is situated on a U-shaped or O-shaped frame arranged on the coupling side of the first arrangement module, and the second coupling structure is located on a U-shaped or O-shaped bar, which are pushed into one another and, in the case of U-shaped frames and bars, are preferably arranged opposite one another. In this case, the frame can also fulfil a protective function for the data and/or energy transmission units if these are arranged within the U-shape or O-shape.

The bar is supported in such a way that the defined distance is a maximum displacement distance corresponding to the raster dimension. If, starting from a locking position in which the first and second protrusions are aligned, the bar is moved by the defined distance or unlocked, the first and second protrusions are moved to an offset position with respect to each other, which corresponds to an unlocking position. In this position, the first and second protrusions can be moved in comb-like fashion through each other and thus the two arrangement modules can be separated in a direction perpendicular to the coupling side and to the locking and unlocking direction.

Preferably, the first protrusions of the first coupling structure of the frame have first ramps facing an unlocking direction of the bar. Alternatively or additionally, the second protrusions of the second coupling structure of the bar may have second ramps facing a locking direction of the bar.

The ramps are located on sides facing each other of the first or second coupling structure, which means that when the bar moves in the locking direction, they may collide, slide along each other and thus ensure that the bar cannot collide laterally with the first coupling structure and block or cant there. Furthermore, the two arrangement modules are pulled towards each other. This is particularly important with regard to any existing electronic interfaces, as these are thereby closed. The fact that the two arrangement modules, during the coupling process according to this embodiment, are moved relative to each other exclusively in a direction perpendicular to the coupling side and are not swiveled or rotated, as would be the case, for example, with a hinge-like arrangement, offers a particular advantage. In this way, it is also possible to use interfaces that are sensitive to misalignment during insertion.

Preferably, the bar has one stop each in its locking direction and/or unlocking direction (displacement directions), which is adapted to come into contact with an associated stop of the second housing part.

By way of example, this stop may be shaped in the form of a projection or a pocket, the ends of which serve as one of the stops in the direction of displacement. In this way, a displacement of the bar can be limited so that, for example, it cannot be displaced beyond the locking or unlocking position and/or cannot fall out of the second arrangement module.

Preferably, a portion of the bar having a marking is exposed when the two arrangement modules are in an unlocked state to provide conspicuous visual feedback regarding the state. Further preferably, the portion of the bar having the marking is covered by the second housing part if the two arrangement modules are in a locked state.

This is especially possible if one end of the bar in the unlocked state protrudes from the housing, e.g. from a slot provided therein, and the corresponding end is marked in color, preferably in signal color. For example, an upper and lower side of the bar can be completely colored, or the material of the bar itself can be selected as colored plastic. It is only important that a surface of the bar, which is exposed in the unlocked state, is located at a conspicuous place for operating personnel to generate a signal effect and immediately catch the eye if locking of the arrangement modules has been forgotten. In the locked state, the portion of the bar having the marking is correspondingly covered or inserted into the arrangement module and thus generates no signal effect. It is also possible to additionally integrate an LED in the corresponding end of the bar to maximize the signal effect. It should be noted that in the present invention the marking is to be distinguished from a simple labeling. A labeling is present, for example, in a case where a button with an arrow or similar is moved from a display labeled "open" to a display labeled "closed", which cannot produce a signal effect in accordance with the marking.

Preferably, an exposed bar lock rotatably mounted in the second housing part is provided for actuation of the bar. The rotation axis of the bar lock can be perpendicular to a housing wall of the second arrangement module, where the bar lock is accessible for a user. By advantage, a rotatable bar lock takes up little space and is easy to operate. The bar lock can preferably be operated by the operating personnel merely by using a simple tool such as a coin, a screwdriver or an insertable lever. Alternatively, a fixed actuating element such as a lever or knob can also be provided.

Preferably, in a direction of rotation of the bar lock, the bar lock respectively has a forwardly and/or rearwardly facing stop which is adapted to come into contact with an associated stop of the second housing part. Further preferred, the bar lock engages in a guiding groove of the bar, with the guiding groove being shaped in such a way that a rotary movement of the bar lock is converted into a linear motion of the bar by means of this guiding groove. The simple geometry of the bar lock makes it easy to manufacture and clean.

The rotary movement of the bar lock can be converted into a pivoting or shifting motion of the bar, for example, by a contact with a suitably shaped guiding groove or supporting surface of the bar. Alternatively, a lever system is also conceivable.

The stops of the bar lock can be provided alternatively or in addition to the stops provided on the bar in order to limit a rotary movement of the bar lock and thus a locking and unlocking movement of the bar. In particular, if the movement of the bar lock is transmitted via a part (e.g. a pin) of the bar lock guided in a guiding groove or support surface, the stops ensure that the bar lock does not overturn and that this contact between bar and bar lock is not released (e.g. that the pin does not slip out of the guiding groove or slip off from the support surface).

Preferably, a portion of the bar lock having the marking is exposed when the two arrangement modules are in an unlocked state to provide conspicuous visual feedback with regard to the state. This is an alternative to the above described variant, where the marking is provided at the end of the bar, which makes it possible to dispense with protruding parts, which can protrude and on which operating personnel can possibly get caught, but which may also be less conspicuous and possibly hidden in the field of vision of a careless operator.

Furthermore, the object is achieved by a medical device, in particular an infusion pump, comprising a housing which forms the modular arrangement system described above, wherein preferably the first arrangement module is a housing cover and the second arrangement module is a housing base.

DETAILED DESCRIPTION

An exemplary embodiment of the present disclosure will be described below on the basis of the corresponding Figures. The same reference symbols designate the same components. The invention is not limited by the exemplary embodiment. Other conceivable embodiments as well as various changes and modifications are contained in the scope of the invention.

Figure 1:
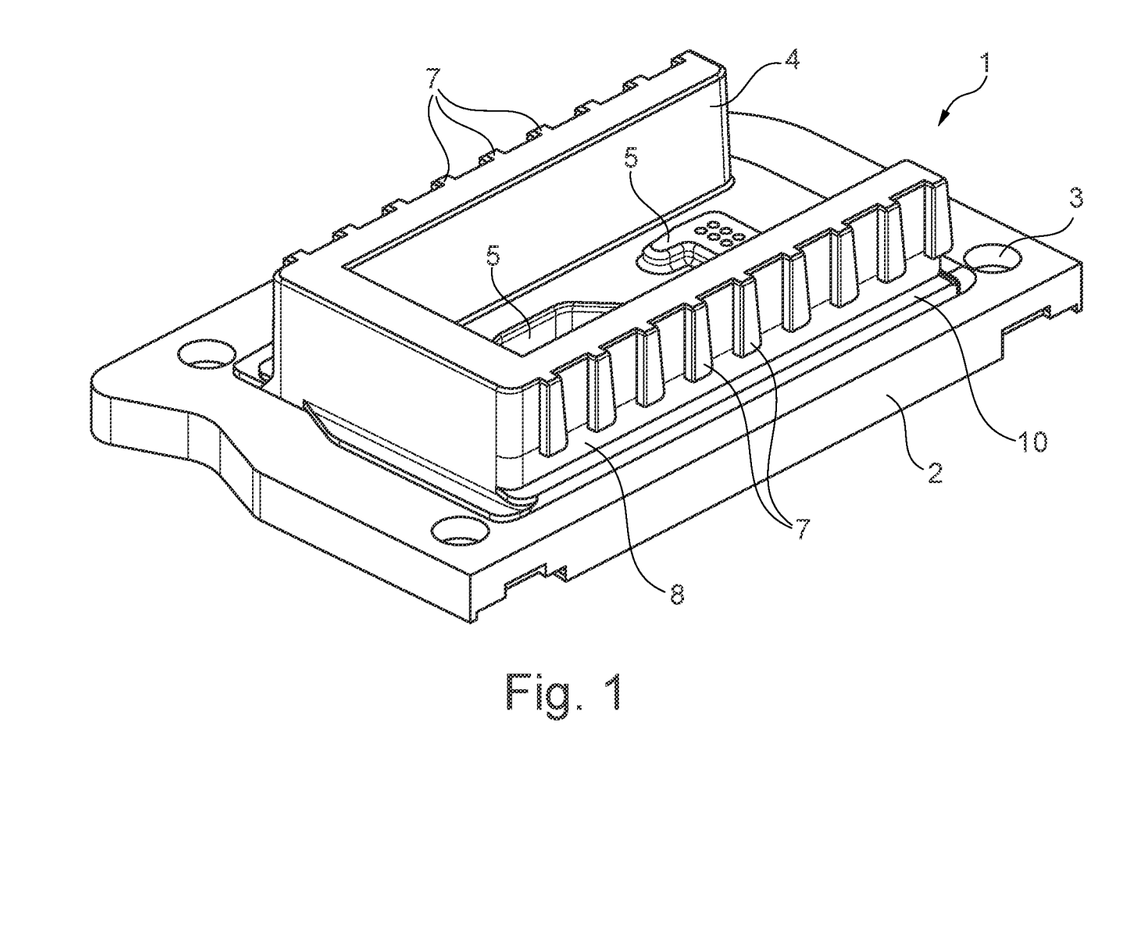
FIG. 1 shows a perspective view of a first housing part according to an embodiment of the present invention.

FIG. 1 shows a perspective view of a first housing part 1, which in this exemplary embodiment is an upper housing part or cover. In principle, however, it may also be a lower housing part. It comprises a horizontal base plate 2 which extends parallel to an x-y plane defined by a coordinate system and has through-holes 3 to be mounted to a basic housing of an associated first arrangement module O1 by means of a screw connection. Instead of the screw connection, other fastening variants are also conceivable, such as a clip, welding or door-like connection, in which the base plate is hinged on one side to the basic housing and locked on the other side.

A U-shaped frame 4 is integrally formed with the base plate 2 and extends vertically from the base plate 2 upwards in the z-direction. In this representation, a base of the U-shape (U-base) of the frame 4 extends in a y-direction and legs of the U-shape (U-legs) of the frame 4 extend in an x-direction. The U-shape of the frame 4 extends almost over the entire width and length of the base plate 2, which is why the two free ends of the U-shape of the frame 4 as well as the ends which are each connected to the U-base of the frame 4 are essentially diametrically opposed to each other on the base plate 2. It should be noted that in the following, the terms "inside" or "facing inwards" and "outside" or "facing outwards" in connection with the U-shape always refer to the inside or outside of the U-shape, i.e. the space between the U-legs or the space outside the U-legs and the U-base.

Within the U-shape of the frame 4 there is space provided for data and/or energy transmission units 5 such as electrical connectors. The frame 4 surrounds the data and/or energy transmission units 5 and protrudes beyond them, thus acting as a protective structure. External surfaces, at least in the x-direction, and possibly also external surfaces facing in the y-direction, of the frame 4 rest against complementary internal surfaces of a second housing part 6 which is attached to a second arrangement module O2 and will be described later, and in this way determine the position of the two housing parts 2, 6 relative to one another at least in the x-direction when the two arrangement modules O1, O2 are mounted to one another. These outer and inner surfaces can be beveled so as to be complementary to each other, so that an upper edge of the outer surfaces is further away from an outer edge of the base plate 2 than a lower edge of the outer surfaces in a plan view of the first housing part 1. In this way, the outer and inner surfaces can serve as centering elements, which facilitate the assembly and precise arrangement of the two housing parts 2, 6.

A first coupling structure 7 is provided on the outside of the U-shaped frame 4. This first coupling structure 7 has a number of first protrusions or ribs which are preferably evenly distributed along the U-legs of the frame 4 in a defined raster with a defined raster dimension. The raster dimension is defined by a width and a distance of the protrusions in the x-direction. A gap 8 is formed between the first coupling structure 7 and the base plate 2 along the U-legs of the frame 4, which serves to accommodate a bar 9 which is supported in the second housing part 6. When the two housing parts 1, 6 are placed on top of each other, the bar 9 is displaceable in relation to both housing parts 1, 6 by a defined distance D (displacement distance) in the x-direction, wherein the displacement in the positive x-direction, i.e. towards the side of the U-base of the frame 4, corresponds to a locking direction and the displacement in the negative x-direction, i.e. towards the side of the free ends of the U-legs of the frame 4, corresponds to an unlocking direction. The displacement distance D of the bar 9 between a locking position and an unlocking position corresponds to the raster dimension of the first coupling structure 7 described above. Around the U-shaped frame 4, in particular along the U-legs of the frame 4, the base plate 2 has a flat protuberance 10 formed integrally therewith, on which the bar 9 slides. In this way, the size of the surface to be reworked for smooth gliding of the bar 9 can be limited, thus saving production costs.

Figure 2:
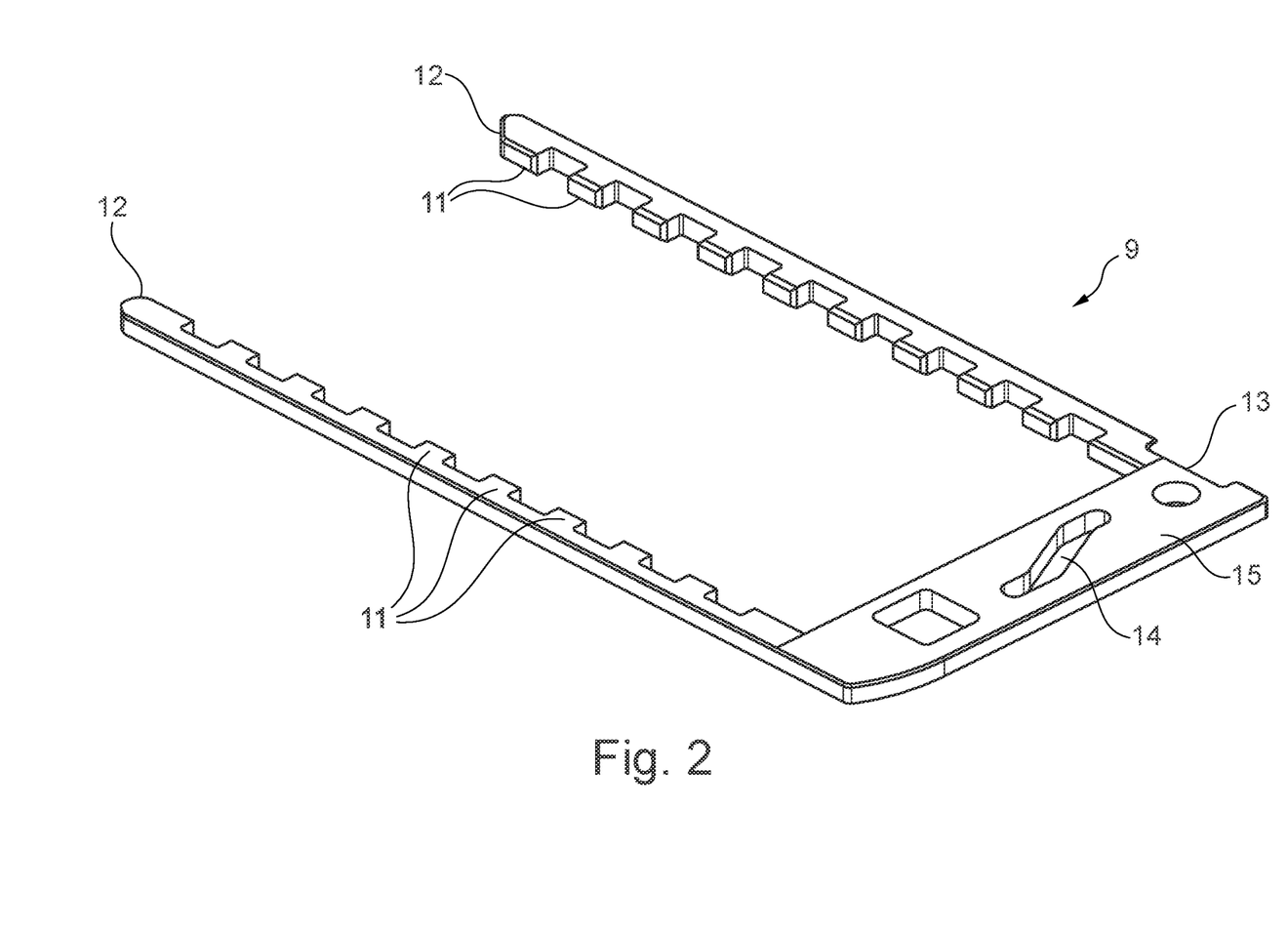
FIG. 2 shows a perspective view of a bar according to the embodiment.

FIG. 2 shows a perspective view of the bar 9, which also has a U-shape with a U-base extending in y-direction and two U-legs extending in x-direction, which U-shape is slightly wider than the U-shape of the frame 4, so that the bar 9 can be pushed over the frame 4. Along the U-legs of the bar 9, facing the interior of the U-shape of the bar 9, a second coupling structure 11 complementary to the first coupling structure 7 is formed, which has a number of second protrusions or ribs uniformly distributed along these U-legs, the width and spacing of which being determined by the above-described raster or raster dimension of the first coupling structure 7. The distance between inwardly facing flanks of the U-legs of the bar 9 or the second coupling structure 11 formed thereon essentially corresponds to the distance between outwardly facing flanks of the U-legs of the frame 4 at the height of the gap 8. Alternatively, the bar and the frame 4 can also be adapted such that the second coupling structure is provided on the outside of the bar and the first coupling structure on the inside of the frame 4.

The free ends of the U-shape of the bar 9 have inclined surfaces 12 or are slanted inwards in such a way that the distance between the inner flanks of the U-legs of the bar 9 increases along the inclined surfaces 12 towards outside. Furthermore, a pocket (notch) 13 is formed on a flank of the bar 9 (outer edge) facing in the y-direction, in this embodiment at the height of the base section, which pocket provides one stop each in the positive x-direction and the negative x-direction. The stops formed by the pocket 13 are intended to come into contact with associated stops formed on the second housing part 6, for example by a projection, and thus to limit a movement of the bar 9 in the x-direction with respect to the second housing part 6.

In a surface of the U-base of the bar 9 extending parallel to the x-y plane, an opening (breakthrough) extending in the z-direction is formed, which serves as guiding groove/guide slot 14. The guiding groove 14 extends in the bar surface along an S-curve. i.e. a first end of the guiding groove is closer to an outer edge of the U-base of the bar 9 and first extends parallel to the outer edge of the U-base (in the y-direction), then follows a curve away from the outer edge of the U-base and then follows a curve in the opposite direction, so that the guiding groove 14 finally extends again in the y-direction at its second end, but has a greater distance to the outer edge of the U-base than at its first end. In principle, the guiding groove 14 can be positioned in the y-direction at any point of the U-base of the bar 9, but it is advantageous if it is arranged in the middle to avoid jamming.

The surface of the U-base of the bar 9 as well as an opposite, lower surface of the U-base have a conspicuous colored marking 15 or are advantageously completely colored. Alternatively, the entire bar can also be colored. As will be explained later in more detail, the bar in its unlocking position protrudes from a slot 16 in the second housing part 6, making the marking 15 conspicuously visible for operating personnel. A simple hint, such as a pointer pointing to an "open" or "closed" symbol, could not fulfil such a signal effect, since only a position of a component changes that looks the same in every condition. The conspicuous marking 15, on the other hand, which is only exposed in the open state and marked in signal colors, is not only a simple indication, but also an attention-grabbing warning which is difficult for operating personnel to overlook, even if they do not pay special attention to it.

Figure 3A:
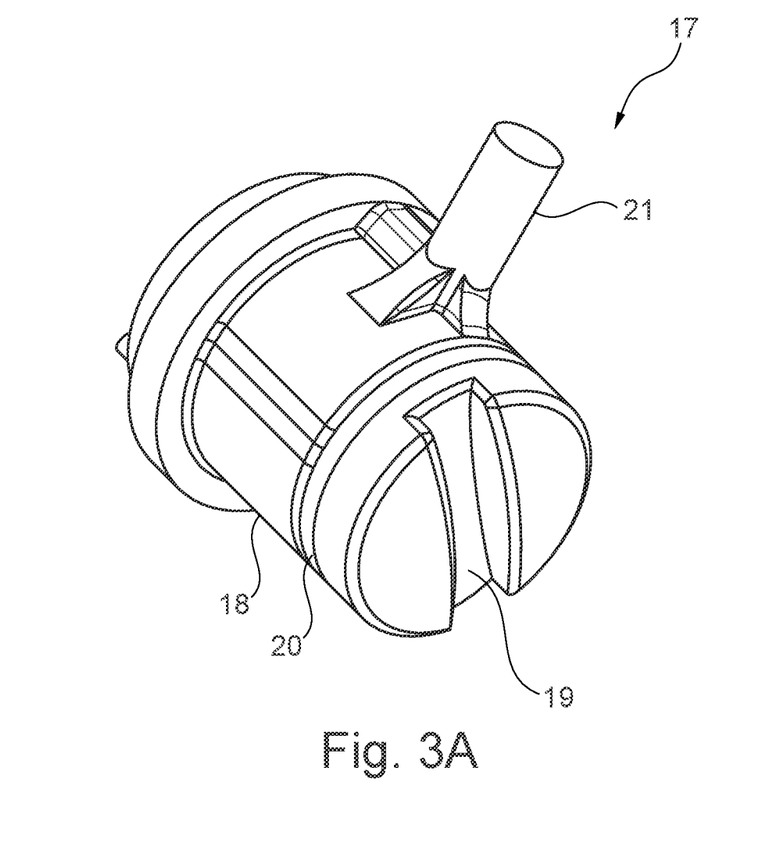
FIGS. 3A/3B show two perspective views of the bar lock according to the embodiment.
Figure 3B:
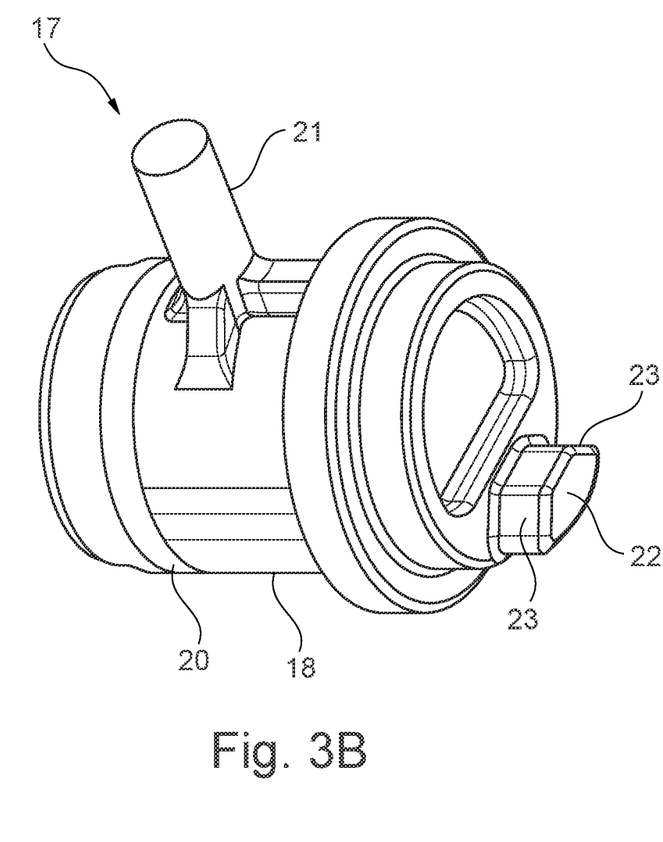

FIG. 3 shows a perspective view of a bar lock 17 (FIG. 3A, left) and a second perspective view of the bar lock 17 seen from another side (FIG. 3B, right). When mounted, the bar lock 17 is rotatably mounted in the second housing part 6. As shown in FIG. 3A, the bar lock 17 has a cylindrical lock body 18 with a tool receiving means 19 on the front for operation of the bar lock 17 by operating personnel. The tool receiving means 19 in this embodiment is a slot that can be operated by a coin or similar, but can alternatively be adapted for any type of tool such as a screwdriver. Alternatively, instead of a tool receiving means, the lock may have a handle that can be operated manually. The advantage of an embodiment having a simple tool receiving means is that the lock does not protrude to the outside and one cannot get caught and injured, overturn the device or even accidentally operate the lock.

On a lateral surface of the lock body 18, preferably directly behind the front face having the tool receiving means 19, there is a groove with an O-ring 20 inserted in it. The O-ring 20 serves on the one hand to seal between the bar lock 17 and the second housing part 6, and on the other hand it generates an increased friction resistance between them, whereby the bar lock 17 is held in its position relative to the second housing part 6 if it is not actuated against the friction resistance.

Behind the groove with the O-ring 20, an actuating pin 21 is provided on the lateral surface of the lock body 18, which extends outwards from the lateral surface in a radial direction of the lock body 18. If the bar lock 17 and the bar 9 are inserted in the second housing part 6, the actuating pin 21 engages in the guiding groove 14 of the bar 9. If the bar lock 17 is rotated, the actuating pin 21 slides along flanks of the S-shaped guiding groove 14, transforming the rotational movement of the bar lock 17 into a linear movement of the bar 9.

As shown in FIG. 3B, an eccentrically arranged nipple/pin 22 is formed on a back side of the lock body 18 opposite to the tool receiving means 19, which, as seen in top view along a central axis of the lock body 18, has a substantially trapezoidal shape with two stop surfaces 23. Alternatively, the nipple 22 can also be realized in the form of a circular section or triangle. The planes in which the two stop surfaces 23 are disposed are arranged facing inwards with respect to the cylindrical base area of the lock body 18, while an optionally curved base side of the trapezoid-like shape faces outwards. The planes of the stop surfaces 23 may intersect in the central axis of the lock body 18, but they may also have deviating angles in relation to it. The stop surfaces 23 of the bar lock 17 are adapted to come into contact with associated stop surfaces 24 of the second housing part 6 and thus to limit a rotational movement of the bar lock 17 to a defined angle, for example between 70° and 100°, advantageously 85° to 90°. This prevents the actuating pin 21 from slipping out of the guiding groove 14 of the bar 9. This effect is also achieved by the stops provided by the pocket 13, described in FIG. 2, on the bar 9, which on the one hand ensures double protection against slipping of the actuating pin 21 out of the guiding groove 14 and on the other hand ensures that any load applied to the bar 9, e.g. by a stroke exerted onto the open bar 9 protruding from the second housing part 6, is not absorbed by the more sensitive actuating pin 21 but by the stops of the bar 9, which is more stable due to its geometry and material selection.

Figure 4:
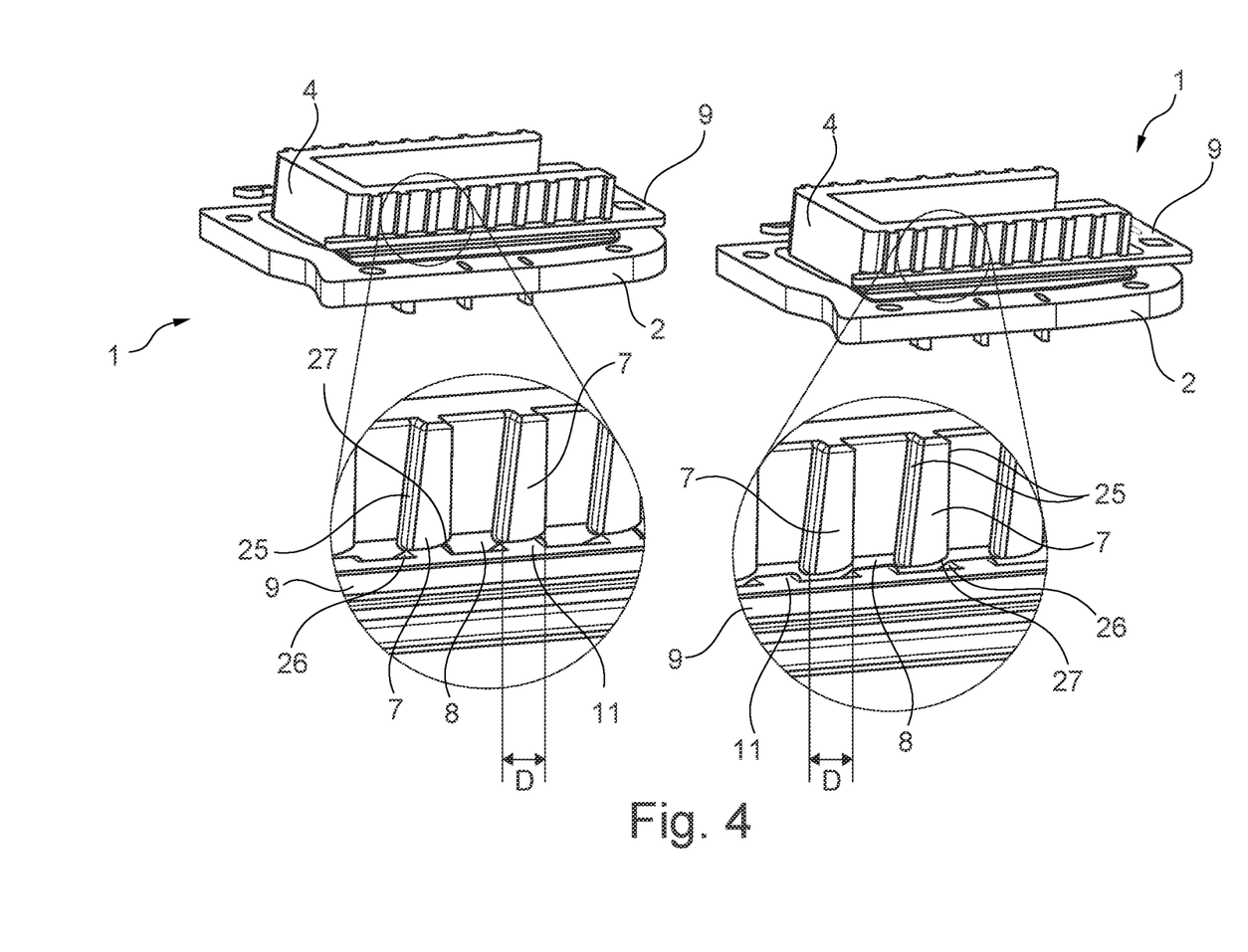
FIG. 4 shows a position of the bar and of the first housing part in relation to each other in the locking position and in the unlocking position.

FIG. 4 shows a position of the bar 9 and of the first housing part 1 in relation to each other in the locking position (left) and in the unlocking position (right) with enlarged detail views of the coupling structures 7, 11. The bar 9 is disposed in the gap 8 of the first housing part 1. In particular, the first and second coupling structure 7, 11 are to be explained in more detail on the basis of said FIG. 4.

It can be clearly seen that the flanks 25 of the individual first protrusions or ribs of the first coupling structure 7 are wedge-shaped. This means that the individual first protrusions do not extend exactly vertically upwards in the z-direction, but have a small angle relative to each other, preferably between 3° and 30°, so that gaps between the first protrusions widen slightly upwards. When the two housing parts 1, 6 are placed on top of each other, the second protrusions of the second coupling structure 11 arranged at the bar 9 and complementary to the first coupling structure 7 push through the gaps between the first protrusions into the gap 8 between the first coupling structure 7 and the base plate 2, with the second protrusions possibly sliding along the flanks 25 of the first protrusions. In this process, the slightly inclined flanges 25 of the first protrusions serve as centering aids or insertion aids for the second protrusions of the second coupling structure 11 of the bar 9.

Furthermore, it can be clearly seen here that at the lower end of the first protrusions, i.e. at their side facing the gap 8, a width of the first protrusions in the x-direction essentially corresponds to the distance between two of the first protrusions, i.e. the width of the gap between them, which in turn corresponds to the raster or raster dimension. Since the raster also determines the width of the second protrusions of the second coupling structure 11 of the bar 9 as well as a width of gaps between two of the second protrusions, as illustrated in FIG. 4, it is clearly visible that the second protrusions of the bar 9 slide during a locking process between the first protrusions of the first coupling structure 7, the bar 9 comes to lie in the gap 8 (unlocking position, right) and is displaced therein in the locking direction relative to the first coupling structure 7, so that in a locking position (left) the second protrusions are suitably positioned under the first protrusions or engage therein and thus prevent the two housing parts 1, 6 from moving away from each other in the z-direction. Due to the fact that the contact or engagement surface between the two coupling structures 7, 11 is distributed over almost the entire width of the housing parts 1, 6 according to the raster, this locking mechanism enables a high stability, resistance and reliability of the connection between the arrangement modules O1, O2 of the arrangement system O.

Furthermore, FIG. 4 shows that the second protrusions of the second coupling structure 11 of the bar 9 are provided with second ramps 26 on a side (upper side) facing the first coupling structure 7 in the locking direction (i.e. towards the free ends of the U-legs of the bar 9). Similarly, first ramps 27 are provided on a side (underside) of the first protrusions facing the second coupling structure 11 or the gap 8 in the direction of unlocking (i.e. facing towards the free ends of the U-legs of the frame 4 and away from the free ends of the U-legs of the bar 9). In this way, the second ramps 26 of the second protrusions of the bar 9 meet the first ramps 27 of the first protrusions of the frame 4 during a locking process, slide off along them and thus contribute to the fact that the bar 9 does not cant but moves under the first protrusions by sliding off. If the bar 9 is pushed under the first protrusions in this way, a force between the two housing parts 1, 6 acting in the z-direction is generated due to the ramps 26, 27, which pulls them together. This helps to reliably connect the data and/or energy transmission units 5.

Figure 5:
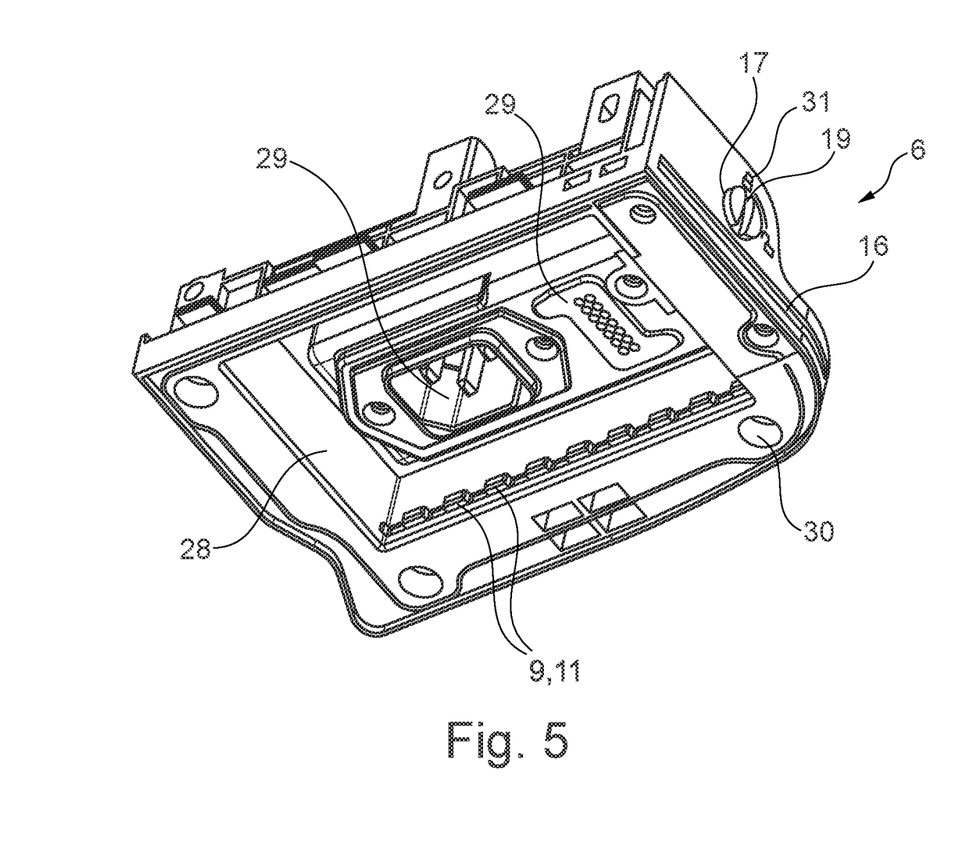
FIG. 5 shows a perspective view of the second housing part according to the embodiment.

FIG. 5 shows a perspective view of the second housing part 6 from below, according to the embodiment, which in this exemplary embodiment is a lower housing part or bottom. In principle, however, it can also be an upper housing part. It is clearly visible that a depression 28 is formed in this second housing part 6, which provides the inner surfaces of the second housing part 6 serving as centering aids and serves to accommodate the frame 4. Furthermore, the data and/or energy transmission units 5 of the first housing part 1 are complemented by data and/or energy transmission units 29 in depression 28. Outside the depression 28, through-holes 30 are provided on the second housing part 6, which serve to fasten it, for example by screws, to the second arrangement module O2.

In the second housing part 6, the bar 9 is mounted so that it can be moved in the x-direction and the bar lock 17 is mounted so that it can rotate. The bar lock 17 with its tool receiving means 19 is exposed on one side of the second housing part 6 so as to be accessible for operating personnel. In addition, at the side of the second housing part 6, next to the tool receiving means 19, a labeling 31 is provided which indicates a locking or unlocking position of the bar lock 17 depending on the angular position of the slot-shaped tool receiving means 19. In addition, the slot 16 is provided at the side of the second housing part 6 next to the tool receiving means 19, in which the U-base of the bar 9 with marking 15 is embedded in the locking position shown in FIG. 5 and protrudes conspicuously in the unlocking position.

Figure 6:
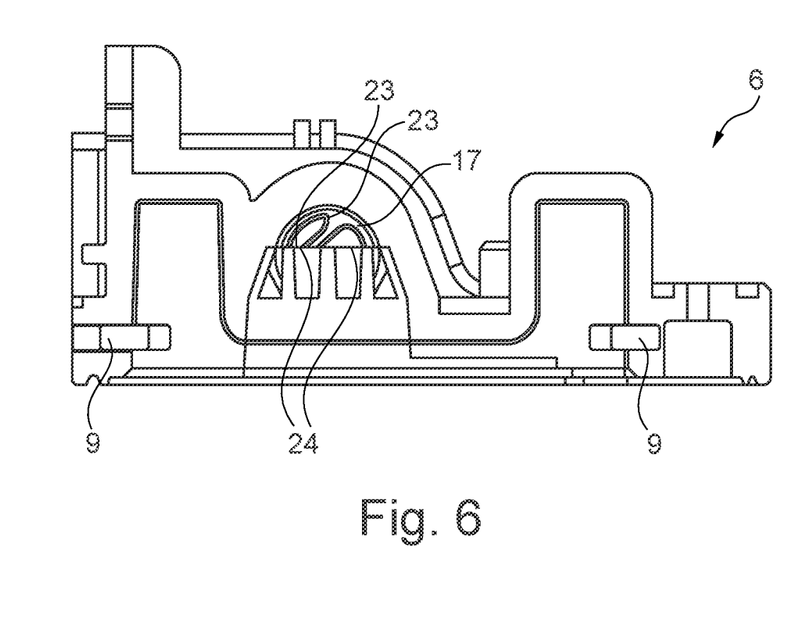
FIG. 6 shows a partial cross-sectional view of the first housing part according to the embodiment, the sectional plane being perpendicular to a direction of movement of the bar.

FIG. 6 shows a cross-section through the second housing part 6, in which the bar 9 and the bar lock 17 are installed, along a section plane which is perpendicular to the x-direction so as to allow an immediate plan view of the bar lock 17 from within the depression 28. In this view, it can be seen that one of the stop surfaces 23 of the nipple 22 contacts one of the associated stop surfaces 24 of the second housing part 6 and the bar lock is thus in an end position, i.e. the bar 9 is either completely locked or unlocked.

Figure 7A:
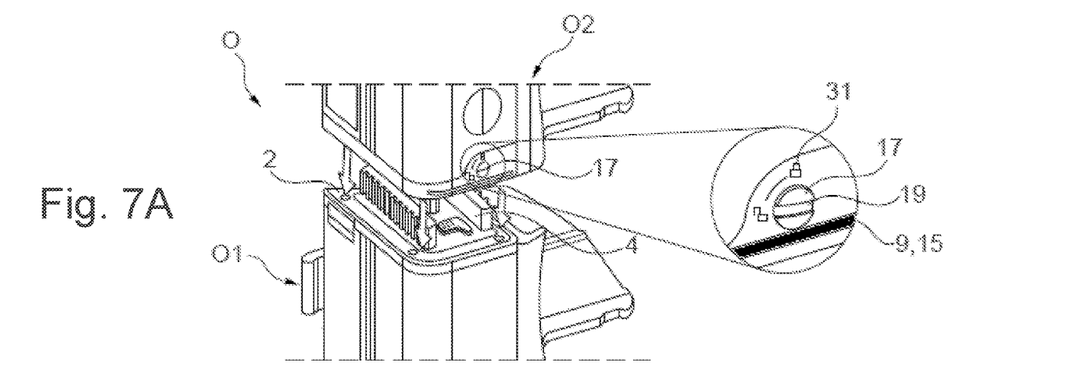
FIG. 7A illustrates an assembly process of two arrangement modules according to the embodiment in a first state.
Figure 7B:
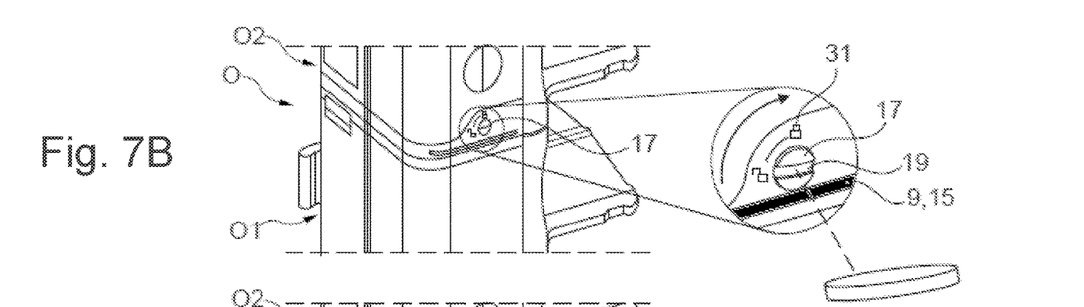
FIG. 7B illustrates an assembly process of two arrangement modules according to the embodiment in a second state.
Figure 7C:
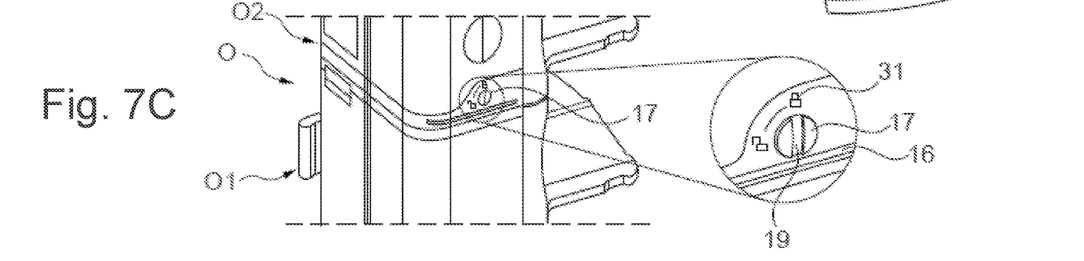
FIG. 7C illustrates an assembly process of two arrangement modules according to the embodiment in a third state.

FIGS. 7A-7C illustrate an assembly process of the two arrangement modules O1, O2 according to the embodiment. FIG. 7A shows the first (lower) and the second (upper) arrangement module O1, O2, which, as illustrated by arrows, are in the process of being placed on top of each other. First, the bar lock 17 is turned to an unlocking position marked by labeling 31, as shown in the enlarged section on the right. Here, the bar 9 carrying the marking 15 (in this Figure the contour filled with black color) protrudes from the slot 16 and thus draws attention to the unlocked state in a conspicuous way. During assembly, the coupling structures 7, 11 are pushed into each other as described above.

In FIG. 7B, the two arrangement modules O1, O2 are placed on top of each other and centered so that they are flush with each other, but are not yet locked, as indicated by the labeling 31 and marking 15. Accordingly, they can still be moved away from each other in the x-direction and separated. The bar 9 is in the gap 8 in this position, but the second protrusions of the second coupling structure 11 are not below the first protrusions of the first coupling structure 7, but are offset relative thereto and do not overlap. In order to lock the arrangement modules O1, O2, a tool exemplarily shown as a coin is inserted into the tool receiving means 19 to operate the bar lock 17 and thus the bar 9.

FIG. 7C shows the locked state of the two arrangement modules O1, O2, which is characterized in that, on the one hand, the tool receiving means 19 of the bar lock 17 points to the corresponding labeling and, in particular, the U-base of the bar 9, which has the marking 15, does not protrude from the slot 16 and thus does not issue a warning signal.

The invention claimed is:

1. A modular arrangement system for arranging at least one medical device, the modular arrangement system comprising at least a first arrangement module and a second arrangement module, the first arrangement module and the second arrangement module configured to be mechanically connected to one another, wherein:
   both the first arrangement module and the second arrangement module have: a first housing part on which a first coupling structure is provided on at least two diametrically opposed sides, and a second housing part;
   wherein the second housing part of the second arrangement module is adapted to be mounted on, below or laterally to the first housing part of the first arrangement module, and at least one of the second housing part of the first arrangement module and the first housing part of the second arrangement module is configured to be coupled to a third arrangement module
   wherein:
   the modular arrangement system comprises a bar rotatably or slidably supported in the second housing part of the second arrangement module for locking the first housing part of the first arrangement module with the second housing part of the second arrangement module, the first coupling structure comprises a raster of first protrusions, the bar comprises a second coupling structure having a complementary raster of second protrusions adapted to engage with the first protrusions in an undercutting manner, and the bar is designed in such a way that, by a singular actuation, the bar engages with the first coupling structure on at least two diametrically opposite sides of the first housing part of the first arrangement module.

2. The modular arrangement system according to claim 1, wherein the bar is configured to be linearly displaced by a defined distance and wherein the raster of first protrusions and complementary raster of second protrusions set the defined distance.

3. The modular arrangement system according to claim 1, wherein
the first protrusions have first ramps facing an unlocking direction of the bar, and/or
the second protrusions have second ramps facing a locking direction of the bar.

4. The modular arrangement system according to claim 1, wherein the bar in a locking direction and/or in an unlocking direction has one stop adapted to come into contact with an associated stop of the second housing part.

5. The modular arrangement system according to claim 1, wherein a portion of the bar comprises a marking that is exposed when the first and second arrangement modules are in an unlocked state to provide conspicuous visual feedback regarding the unlocked state.

6. The modular arrangement system according to claim 5, wherein
the portion of the bar having the marking projects from an opening of the second housing part when the first and second arrangement modules are in the unlocked state, and
the portion of the bar having the marking is covered by the second housing part when the first and second arrangement modules are in a locked state.

7. The modular arrangement system according to claim 1, wherein a bar lock is exposed and rotatably mounted in the second housing part, the bar lock configured for actuating the bar.

8. The modular arrangement system according to claim 7, wherein the bar lock, in a direction of rotation of the bar lock, comprises a respectively forwardly and/or rearwardly facing stop adapted to come into contact with an associated stop of the second housing part.

9. The modular arrangement system according to claim 7, wherein the bar lock engages in a guiding groove of the bar, and the guiding groove is shaped such that a rotational movement of the bar lock is converted via the guiding groove into a linear movement of the bar.

10. The modular arrangement system according to claim 7, wherein a portion of the bar lock comprises a marking that is exposed when the first and second arrangement modules are in an unlocked state to provide conspicuous visual feedback regarding the unlocked state.

11. A medical device comprising a housing defined by the modular arrangement system according to claim 1, wherein a portion of the first arrangement module covers the medical device and a portion of the second arrangement module is under the medical device.

12. The medical device according to claim 11, wherein the medical device is an infusion pump.

13. The modular arrangement system according to claim 1, wherein the bar is U-shaped.

14. The modular arrangement system according to claim 1, wherein:
the first coupling structure comprises a first base plate, and a frame extending in a first direction away from the first base plate and defining the at least two diametrically opposite sides of the first housing part;
the second housing part of the second arrangement module comprises a depression configured to receive the frame upon moving the frame along the first direction into the depression; and wherein the bar
is configured to slide in a second direction that is perpendicular to the first direction between an unlocked position in which the frame is free to move along the first direction relative to the depression, and a locked position in which the frame is retained in the depression by the bar.

15. The modular arrangement system according to claim 14, wherein:
when the bar is in the unlocked position the complementary raster of second protrusions is offset from the raster of first protrusions along the second direction; and
when the bar is in the locked position the complementary raster of second protrusions is aligned with the raster of first protrusions along the second direction.

16. The modular arrangement system according to claim 14, wherein:
the raster of first protrusions are located on the at least two diametrically opposite sides of the first housing part; and
the bar comprises a first leg extending along the second direction and a second leg extending along the second direction and spaced from the first leg to define an opening between the first leg and the second leg, and the complementary raster of second protrusions extend from the first leg and the second leg into the opening.

17. The modular arrangement system according to claim 16, wherein:
the bar comprises a body portion connecting the first leg and the second leg, and the body portion comprises a groove; and
the second housing part comprises an actuating pin movably mounted to the second housing part and extending into the groove, wherein the actuating pin is configured to move the bar between the unlocked position and the locked position by movement of the actuating pin in the groove.

18. The modular arrangement system according to claim 1, wherein the second housing part comprises:
a second base plate;
a recess extending in a first direction from the second base plate; and
a slot extending in a second direction that is perpendicular to the first direction;
wherein the bar is configured to slide within the slot in the second direction between an unlocked position in which the bar does not secure the first housing part of the first arrangement module to the second housing part of the second arrangement module, and a locked position in which the bar secures the first housing part of the first arrangement module to the second housing part of the second arrangement module.

19. The modular arrangement system according to claim 18, wherein the second housing part comprises:
- a lock body extending into the second housing part adjacent to the slot and rotatable about an axis that is perpendicular to the first direction; and
- an actuating pin extending radially from the lock body and into engagement with the bar;
- wherein the lock body is rotatable about the axis to move the actuating pin and thereby move the bar between the unlocked position and the locked position.

* * * * *